United States Patent
Van Valen (10) Patent No.: US 8,603,079 B2
(45) Date of Patent: *Dec. 10, 2013

(54) APPRATUS FOR TREATING HYPEROPIA AND PRESBYOPIA VIA LASER TUNNELING

(71) Applicant: Biolase, Inc., Irvine, CA (US)

(72) Inventor: Marcia Angela Van Valen, Aliso Viejo, CA (US)

(73) Assignee: Biolase, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/757,169

(22) Filed: Feb. 1, 2013

(65) Prior Publication Data
US 2013/0144279 A1 Jun. 6, 2013

Related U.S. Application Data

(60) Continuation of application No. 12/975,202, filed on Dec. 21, 2010, now Pat. No. 8,366,702, which is a continuation of application No. 11/980,889, filed on Oct. 30, 2007, now Pat. No. 7,867,223, which is a division of application No. 11/410,564, filed on Apr. 24, 2006, now Pat. No. 7,878,204.

(60) Provisional application No. 60/673,966, filed on Apr. 22, 2005.

(51) Int. Cl.
A61B 18/20 (2006.01)
(52) U.S. Cl.
USPC .............................................. 606/5; 606/10
(58) Field of Classification Search
USPC ............ 606/4–6, 10–13; 607/88, 89; 128/898
See application file for complete search history.

(56) References Cited

U.S. PATENT DOCUMENTS

| 4,526,171 | A  | 7/1985  | Schachar      |
| 5,722,952 | A  | 3/1998  | Schachar      |
| 6,149,643 | A  | 11/2000 | Herekar et al.|
| 6,263,879 | B1 | 7/2001  | Lin           |
| 6,575,962 | B2 | 6/2003  | Hohla         |
| 6,622,729 | B1 | 9/2003  | Peyman        |
| 6,706,036 | B2 | 3/2004  | Lai           |

(Continued)

FOREIGN PATENT DOCUMENTS

| WO | WO9201430    | 2/1992  |
| WO | WO0236029    | 5/2002  |
| WO | WO2005096766 | 10/2005 |

OTHER PUBLICATIONS

Office Action dated Jun. 10, 2013 from related/corresponding Canadian Patent Appl. No. 2609339, entitled, "Method for Treating Hyperopia and Presbyopia via Laser Tunneling".

*Primary Examiner* — Ahmed Farah
(74) *Attorney, Agent, or Firm* — Jones Day (57) ABSTRACT

A method for treating presbyopia utilizes an Erbium based, pulsed laser to sever sub-conjunctival strictures located within the scleral matrix of the eye. Introduction of treatment energy into the scleral matrix increases or facilitates an increase in accommodation, thereby mitigating the effects of presbyopia. The treatment energy can be directed into the scleral matrix to form tunnel ablations in and through the strictures of the scleral matrix. The tunnel ablations can enhance the accommodation of the patient's eye, enabling the eye to refocus at near distances while not losing its ability to focus at a distance.

5 Claims, 8 Drawing Sheets

(56) References Cited

U.S. PATENT DOCUMENTS

| | | |
|---|---|---|
| 6,824,540 B1 | 11/2004 | Lin |
| 6,887,261 B1 | 5/2005 | Peyman |
| 7,033,381 B1 | 4/2006 | Larsen |
| 7,146,983 B1 | 12/2006 | Hohla et al. |
| 7,867,223 B2 | 1/2011 | Van Valen |
| 7,878,204 B2 | 2/2011 | Van Valen |
| 8,366,702 B2 * | 2/2013 | Van Valen ............ 606/5 |
| 2001/0029363 A1 | 10/2001 | Lin |
| 2003/0139737 A1 | 7/2003 | Lin |
| 2003/0220630 A1 | 11/2003 | Lin et al. |
| 2004/0006332 A1 | 1/2004 | Black |
| 2004/0078009 A1 | 4/2004 | Lin |
| 2005/0043722 A1 | 2/2005 | Lin |
| 2007/0123844 A1 | 5/2007 | Henry |

\* cited by examiner

Fig. 1 stricture pre-laser
(sclerotic)

Fig. 2a post-layer lysis

APPRATUS FOR TREATING HYPEROPIA AND PRESBYOPIA VIA LASER TUNNELING

CROSS-REFERENCE TO RELATED APPLICATIONS

This application is a continuation of U.S. application Ser. No. 12/975,202, filed Dec. 21, 2010, which is a continuation of U.S. application Ser. No. 11/980,889, filed Oct. 30, 2007 and entitled METHODS FOR TREATING HYPEROPIA AND PRESBYOPIA VIA LASER TUNNELING, which is a divisional of U.S. application Ser. No. 11/410,564, filed Apr. 24, 2006 and entitled METHODS FOR TREATING HYPEROPIA AND PRESBYOPIA VIA LASER TUNNELING, which claims priority to U.S. Provisional Application No. 60/673,966, filed Apr. 22, 2005 and entitled METHOD AND APPARATUS FOR TREATING HYPEROPIA AND PRESBYOPIA VIA LASER TUNNELING, the entire contents all of which are hereby incorporated by reference.

BACKGROUND OF THE INVENTION

1. Field of the Invention

The present invention relates generally to medical devices and procedures and, more particularly, to devices and procedures for treating hyperopia and presbyopia of the eye using laser tunneling.

2. Description of Related Art

A common ophthalmologic condition relating to focusing disorders is known as hyperopia. Hyperopia, or farsightedness, relates to an eyesight refractive abnormality whereby near objects appear blurred or fuzzy as a result of light rays being brought to focus behind the retina of the eye. One variation of hyperopia is presbyopia, which typically is associated with a person's lack of capacity to focus at near distances and which tends to develop and progress with age. Regarding this progression, presbyopia is thought to advance as the eye progressively loses its ability to accommodate or focus sharply for near vision with increasing age of the person. Accordingly, the condition of presbyopia generally signifies a universal decrease in the amplitude of accommodation of the affected person.

Hyperopia can be treated surgically using techniques including corneal interventions, such as reshaping a surface curvature of the cornea located inside of the limbus area, and non-corneal manipulations, such as altering properties of the sclera located outside of the limbus area, ciliary muscle, zonules, or lens. An example of the former treatment can comprise ablating the surface of the cornea itself to form a "multifocal" arrangement (e.g., distance vision in one eye and reading vision in another eye according to a treatment plan referred to as monovision) facilitating viewing by a patient of both near and far objects, and an example of the latter treatment can comprise introducing kerfs into portions of the sclera to thereby increase accommodation. An example of the latter treatment is disclosed in U.S. Pat. No. 6,263,879, wherein incisions are formed in the sclera beneath the conjunctiva.

SUMMARY OF THE INVENTION

Methods of the present invention for treating hyperopia, such as hyperopia conditions involving, in particular, presbyopia, utilize sources of ablation, such as electromagnetic energy emitting devices, to implement non-corneal manipulations. According to these methods, the sources of ablation can be activated to direct energy onto the sclera of the eye to treat presbyopia, wherein the energy affects at least one property of the sclera and results in an enhancement in an accommodation of the eye.

The source of ablation can comprise a source of electromagnetic energy, such as a laser. In certain implementations, the laser is an Erbium based, pulsed laser which emits treatment energy, such as optical energy, toward the sclera and into the scleral matrix of the eye, to sever sub-conjunctival strictures located within the scleral matrix of the eye. Introduction of the treatment energy into the scleral matrix can increase or facilitate an increase in accommodation of the eye, thereby mitigating the effects of presbyopia.

The treatment energy can be directed into the scleral matrix to form tunnel ablations in and through the sub-conjunctival strictures of the scleral matrix. Augmentation of the accommodation of the patient's eye by way of the impartation of tunnel ablations into the sub-conjunctival strictures of the scleral matrix can enable the eye to refocus at near distances while not losing its ability to focus at a distance.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112.

Any feature or combination of features described herein are included within the scope of the present invention provided that the features included in any such combination are not mutually inconsistent as will be apparent from the context, this specification, and the knowledge of one skilled in the art. In addition, any feature or combination of features may be specifically excluded from any embodiment of the present invention. For purposes of summarizing the present invention, certain aspects, advantages and novel features of the present invention are described. Of course, it is to be understood that not necessarily all such aspects, advantages or features will be embodied in any particular implementation of the present invention. Additional advantages and aspects of the present invention are apparent in the following detailed description and claims that follow.

DETAILED DESCRIPTION OF THE INVENTION

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale unless stated otherwise. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by claims. It is to be understood and appreciated that the method steps and structures described or incorporated by reference herein do not cover complete procedures for the implementations described herein. The present invention may be practiced in conjunction with various medical techniques and devices that are conventionally used in the art, and only so much of the commonly practiced structures and method steps are included herein as are necessary to provide an understanding of the present invention.

As used herein, "accommodation" refers to the ability to change focus from distant objects to near objects, which ability tends to diminish with age.

As used herein, "choroid" refers to the highly vascular layer of the eye beneath the sclera.

As used herein, "ciliary muscle" refers to a muscular ring of tissue located beneath the sclera and attached to the lens via zonules.

As used herein, "conjunctiva" refers to the thin, transparent tissue covering the outside of the sclera.

As used herein, "cornea" refers to the clear central front tissue of the eye which can be considered to be a key component of the focusing system.

As used herein, "surgical limbus" refers to the boundary where the cornea meets the sclera.

As used herein, "retina" refers to the light-sensitive layer of tissue that lines the back of the eyeball and sends visual impulses through the optic nerve to the brain.

As used herein, "sclera" refers to the outer supporting structure, or "the white," of the eye.

As used herein, "stricture" refers to an area where a tube in the body is too narrow. When diameters of the fibrous sheaths, which surround tendons within the sclera, become attenuated, they are referred to as strictures.

As used herein, "tunnel ablation" refers to a relatively large incision, having a rounded, u-shaped, or flattened bottom rather than a v-shaped bottom surface, formed within or through the sclera.

As used herein, "tunneling" refers to the creation of tunnel ablations, and "laser tunneling" refers to creation of the same using a laser.

As used herein, "vitreous body" refers to the clear colorless transparent jelly that fills the eyeball posterior to the lens and that is enclosed by a delicate hyaloid membrane.

As used herein, "zonules" refers to a circular assembly of radially directed collagenous fibers that are attached at their inner ends to the lens and at their outer ends to the ciliary muscle.

An inability of the eye to focus sharply on nearby objects, called "presbyopia," is associated with advancing age and typically entails a decrease in accommodation. Introduction of treatment energy (e.g., laser ablation), according to any of the implementations described herein, may enhance or facilitate an increase in accommodation, thereby mitigating effects of presbyopia. In typical embodiments, introduction of treatment energy to the scleral tissue can increase the accommodation of the eye (e.g., of the ciliary body) to thereby allow the presbyopic patient to see both near and far.

In accordance with various aspects of the present invention, an accommodation can be augmented via introduction of a plurality of "tunnel ablations," meaning incisions or trenches formed (e.g., via ablation) in and through the sclera. The tunnel ablations may be formed by delivering treatment energy from an external location toward the eye. The delivered treatment energy may facilitate formation of tunnel ablations as described herein.

Regarding augmentation of accommodation via formation of tunnel ablations in the sclera, the sclera may be treated (e.g., lased) to form tunnel ablations therein or therethrough, taking care to attenuate or avoid a distortion of optical characteristics of the eye in the process. In an exemplary implementation, sizes, arrangements, depths, and/or other characteristics of the tunnel ablations can be adjusted so as, for example, to increase an accommodation (e.g., flexibility) of the eye. Following treatment, the eye may be better able to change shape and focus. For instance, according to certain implementations, tunnel ablations may be created with, for example, a micro-drill, laser, or incising instrument. In other instances, alternative or additional tunnel ablations may be either similarly formed in the sclera or formed using means different from that used to form the mentioned tunnel ablations, in the same or different locations, at the same or other points in time, and/or with the same or different sizes or shapes as disclosed herein.

Methods for treating hyperopia, and in particular, presbyopia, utilize sources of ablation, such as electromagnetic energy emitting devices, to implement non-corneal manipulations. According to the methods, the sources of ablation can be activated to direct energy onto the sclera of the eye to treat presbyopic conditions, wherein the energy affects at least one property of the sclera and results in an enhancement in an accommodation of the eye. For instance, energy can be delivered from the source of ablation onto the sclera in at least one vicinity of the sclera that does not contact a surgical limbus of the eye. The source of ablation can comprise a source of electromagnetic energy, such as a laser. In certain implementations, the laser is an Erbium based, pulsed laser which emits treatment energy, such as pulsed optical energy, toward the sclera and into the scleral matrix of the eye, to sever sub-conjunctival strictures located within the scleral matrix of the eye. Introduction of the treatment energy into the scleral matrix can increase, or facilitate an increase in, accommodation of the eye, thereby mitigating the effects of presbyopia. The treatment energy can be directed into the scleral matrix to form predetermined tunnel-ablation formations in and through the sub-conjunctival strictures of the scleral matrix. Augmentation of the accommodation of the patient's eye by way of the impartation of tunnel ablations into the sub-conjunctival strictures of the scleral matrix can enable the eye to refocus at near distances while not losing its ability to focus at a distance.

Figure 1:
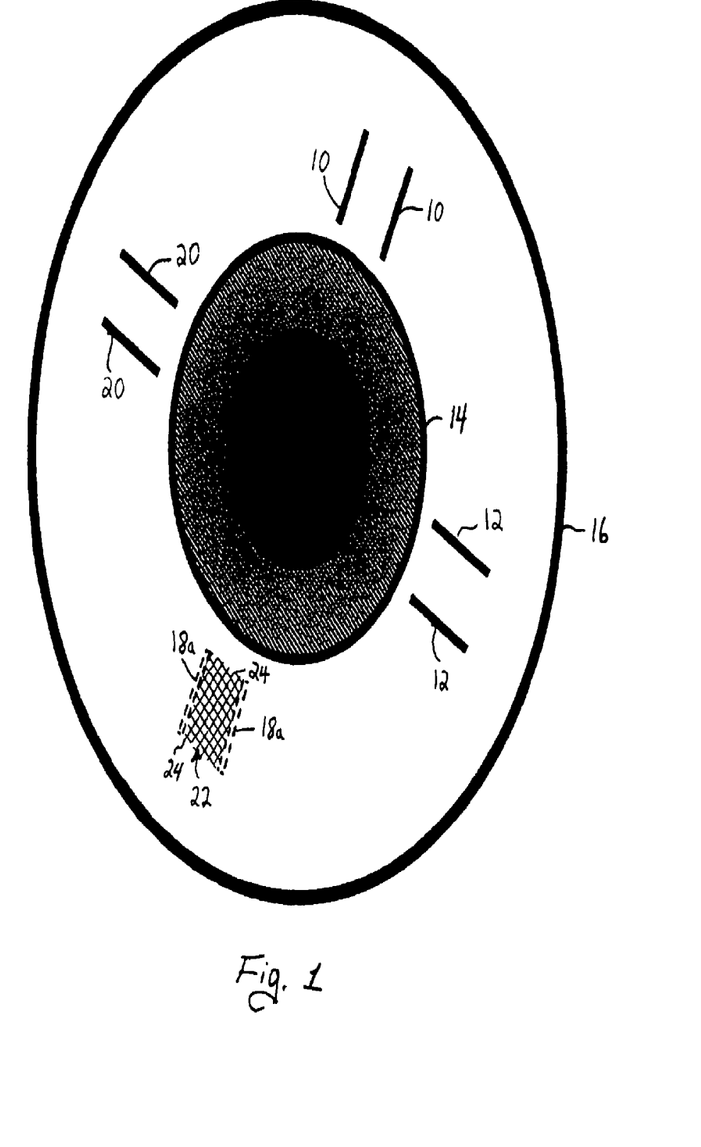
FIG. 1 is a plan view of an anterior portion of the eye, having tunnel ablations formed within the scleral tissue thereof in accordance with an implementation of the present invention, wherein tunnel-ablation areas are depicted in relation to both regions of tissue sclerosis and concomitant strictures that are to be released.

Referring more particularly to the drawings, FIG. 1 shows a schematic plan view of an eye of a patient. In accordance with an aspect of the present invention, areas 10, 12, 18a and 20 of tunnel-ablation placement are generated on and in portions of the sclera containing undesirable strictures, which have resulted from age-induced sclerosis and which have lead to a loss of elasticity of the affected portions of the eye. The plan view of FIG. 1 shows an anterior portion of the eye having a plurality of sets or groupings of tunnel ablations formed within the scleral tissue thereof in accordance with an exemplary implementation of the present invention, wherein tunnel-ablation areas are placed in relation to regions of tissue sclerosis and also in relation to concomitant strictures that are to be released for treatment of presbyopia. The releasing of such strictures in the sclera can lead to greater elasticity of the tissues of the eye and enhanced accommodation of the eye.

According to a broad aspect of the present invention, one or more of the tunnel ablations may be implemented as described herein using various forms of treatment energy, such as electromagnetic radiation (e.g., ablating optical energy, thermal optical energy, blood-coagulating optical energy, and combinations thereof). Typical systems for providing treatment energies may comprise handpieces coupled to one or more of an electromagnetic energy source such as a laser (e.g., a diode laser) having a predetermined wavelength and a predetermined pulse, a cautery device with a predetermined setting that interacts with desired parts of the eye to form tunnel ablations, and combinations thereof.

In very broad implementations of the present invention, electromagnetic energy devices may comprise, for example, lasers having all wavelengths, such as lasers having wavelengths ranging, for example, from about 0.15 microns to about 3.2 microns. Particular implementations of lasers for use on the sclera may comprise Er:YAG, Er:YSGG, Er, Cr:YSGG, or CTE:YAG lasers operated at exemplary wavelengths ranging from about 2.69 microns to about 2.8 microns, and about 2.94 microns. Other implementations of lasers may include XeCl excimer lasers operated at an exemplary wavelength of about 308 nm; frequency-shifted solid state lasers operated at exemplary wavelengths of about 0.15 microns to about 3.2 microns; excimer lasers of ArF operated at an exemplary wavelength of about 93 nm; harmonic generations of Nd:YAG or Nd:YAL or Ti:sapphire lasers operated at exemplary wavelengths of about 190 nm to about 220 nm; CO lasers operated at a wavelength of, for example, about 6.0 microns and carbon dioxide lasers operated at a wavelength of, for example, about 10.6 microns; diode lasers operated at exemplary wavelengths of about 0.8 microns to about 2.1 microns; gas lasers operated at exemplary wavelengths of about 2.6 microns to about 3.2 microns; and other gas or solid state lasers including flash-lamp and diode lasers operated at exemplary wavelengths of about 0.5 microns to about 10.6 microns; and optical parametric oscillation (OPO) lasers operated at exemplary wavelengths of about 2.6 microns to about 3.2 microns. Exemplary wavelengths ranging from 2.78 microns to 2.94 microns have been found to be effective in at least some aspects in forming the tunnel ablations of the present invention.

A preferred implementation, which has been found to be particularly effective in facilitating the formation of tunnel ablations, is a 2.78 micron wavelength emitted by an Er, Cr:YSGG laser. As distinguished from the optical energy emitted from, for example, an Er:YAG, the emission of an Er, Cr:YSGG laser has been found, perhaps as a partial result of its relative coagulation capability, to be effective in forming desired tunnel ablations of the present invention.

Treatment energy in the form of laser radiation can be directed over the sclera of the eye in predetermined patterns to form tunnel ablations having depths of 91% to 100% of the sclera thickness (e.g., about 500 to 700 microns) and, in certain exemplary embodiments, depths between about 95% and 100% of the sclera thickness. Operating parameters for the laser (e.g., an Er, Cr:YSGG laser) can be 0.5 watts to 3.0 watts with continuous-wave (CW) energy or pulsed energy having a relatively high peak energy. For example, the laser can have a repetition rate of to 100 Hz. Exemplary laser energy per pulse values can range from about 0.1 mJ to about 50 mJ, depending on, for example, the pulse duration and the laser beam spot size. Typical laser pulse widths may range from about 100 nanoseconds to about 1000 microseconds. The areas to be treated can be pre-traced with a vascular laser or even a long-pulse configured Er, Cr:YSGG, or a long-pulse configured Er:YAG, to minimize bleeding and/or improve or enable formation of the tunnel ablations.

The depth or depths of the tissue(s) being affected (i.e., depth of sclera) should be accurately determined and monitored. In the context of manual generation of tunnel ablations, a surgeon may observe a color change of, for example, the scleral tissue being treated to determine when the tissue-treatment depth reaches a desired level. For procedures on the sclera, the surgeon may, for example, cease the forming or cutting of a tunnel ablation when a hue (which may be more pronounced in the context of optical ablating rather than scalpel cutting) begins to change at the bottom of the tunnel ablation being formed. A darkening of hue (e.g., to a blue, violet, or dark brown) as tissue is affected (e.g., removed) at the bottom of the tunnel ablation may indicate, for example, less remaining sclera and a greater exposure of the underlying layer (e.g., the vascularised choroid and/or ciliary muscle), at which time the surgeon may decide to slow or stop formation of that tunnel ablation. A chamber maintainer, for forming or facilitating the formation of tunnel ablations may be used, wherein a purpose of the chamber maintainer may be to assure that proper pressure is maintained in the eye so that a prolapse or a perforation does not occur in the choroid during formation of the tunnel ablations.

Exemplary laser beam spot sizes, according to very broad implementations of the present invention, can range from about 0.4 mm up to about 1.5 mm. Relatively large spot sizes, such as spot sizes greater than 800 microns, have been found to be the most effective in forming the tunnel ablations of the present invention. A preferred implementation, which has been found to be effective in facilitating the formation of tunnel ablations, uses a spot size of about 1000 microns. Spot sizes ranging from this 1000 micron diameter to about 1500 microns have been found to be particularly effective in facilitating the formation of tunnel ablations of the present invention. These relatively large spot sizes in accordance with the present invention can facilitate more complete ablations of stricture formations and/or better post-surgery results. The relatively large spot sizes can facilitate generation of optimally-shaped tunnel ablations (e.g., having relatively large, rounded, u-shaped or flattened bottom surfaces), which, in turn, advantageously, can reduce healing thereby promoting more longevenous and successful presbyopic treatments.

While larger diameter fiber tips, corresponding to commensurately larger spot sizes (e.g., 900-1500 micron diameter fiber tips generating 900-1500 micron diameter spot sizes), are typically preferred, it can in certain instances be possible to implement smaller diameter fiber tips, such as 400-600 micron diameter fiber tips, upon the introduction of other modifications or compensating factors (e.g., techniques or structures) to the system. For instance, it may be possible to obtain incisions, which may resemble in some ways tunnel-ablations, with a 400 micron fiber tip, upon the provision of a modified output end of the fiber tip. According to one such implementation, a fiber tip may be provided, having a cone-shaped output end with the point of the cone flattened to form a plane perpendicular to a longitudinal axis of the fiber tip. In other words, the output tip can comprise a truncated-cone shape wherein, rather than the point of a cone, a planar surface is disposed at the distal end for outputting radiation. The pointed end of the conical tip, which in a typical embodiment is centered on the longitudinal optical axis of the fiber optic, can be polished flat to yield a planar output surface so that light traveling along the optical axis exits the planar output surface and continues to travel, unrefracted, along the optical axis. Thus, in the described implementation, the planar output surface is oriented to be perpendicular with, and to intersect with, the longitudinal axis of the fiber optic.

As a few examples, a shaped fiber optic tip having a diameter of about 400 microns may be formed (e.g., polished) to have a truncated planar output surface of about 100 microns in diameter wherein light exiting from the truncated planar surface and from the non-truncated conical surface is distributed in such a way as to promote the formation of incisions resembling in some ways (e.g., tending to have, slightly, or relatively, flat or curved bottom surfaces) the tunnel ablations of the present invention. Similarly, but to a substantially or much more desirable end, a shaped fiber optic tip having a diameter of about 600 microns may be formed (e.g., polished) to have truncated planar output surfaces of about 150 microns in diameter, wherein light exiting from the truncated planar surface and from the non-truncated conical surfaces is distributed in such a way as to promote a more pronounced resemblance of the tunnel ablations of the present invention with their relatively flat or curved bottoms. Furthermore, a much better result, still, can be achieved with a shaped fiber optic tip having a diameter of about 800 microns formed (e.g., polished) to have a truncated planar output surface of about 200 microns in diameter, wherein light exiting from the truncated planar surface and from the non-truncated conical surfaces is distributed in such a way as to promote the formation of structures resembling in some ways the tunnel ablations of the present invention with flattened or curved bottoms. A shaped fiber optic tip having a diameter of about 1000 microns formed (e.g., polished) to have a truncated planar output surface of about 250 microns in diameter can be implemented in a preferred embodiment, wherein light exiting from the truncated planar surface and from the non-truncated conical surfaces is distributed in such a way as to promote the formation of optimal tunnel ablations having somewhat flat or curved bottom surfaces.

According to other embodiments, the fiber tips may comprise, in addition to typical truncated-cylinder output ends (i.e., standard, cylindrically-shaped tips) with planar output surfaces, reverse conical output ends, conical output ends, round output ends, curved output ends, or tapered output ends, with, in certain embodiments, any of these output ends being partially truncated as discussed above. In the above or modified embodiments, the delivery systems (e.g., tips) may comprise, for example, sapphire or quartz, may be coated with, for example, a tantalum substance or covered with a metal for protection, may be configured for single or multi-use, and/or may be either sterile or non-sterile but capable of being sterilized. Also, one or more of the handpiece and the delivery system in general, or any part thereof, may comprise hollow-waveguide, mirrored, geranium oxide, sapphire or quartz components, and may further comprise autoclave, ethylene oxide (eto), gas, or other sterilizable substances.

Formation of tunnel ablations in the sclera as depicted in FIG. 1, using, for example, a laser, can be accomplished by separating the conjunctiva from the sclera. Separation of the conjunctiva from the sclera typically comprises temporarily removing or pulling-back the patient's conjunctiva, using forceps and scissors and/or one or more of scalpels, cautery, plasma, and laser methods, followed by the actual non-corneal manipulations (e.g., forming tunnel ablations in the sclera). While being formed almost entirely of collagen, the conjunctiva is vascular and thus should be handled carefully, for example, to minimize bleeding. The conjunctiva may be, for example, ballooned with a fluid in one embodiment. For instance, a fluid may be inserted beneath the conjunctiva, to thereby separate the conjunctiva from the underlying sclera. Such a separation can be achieved, for example, by injecting a fluid, such as an epinephrine-based fluid, therebetween via a needle entry point in a vicinity of the surgical limbus.

Figure 7:
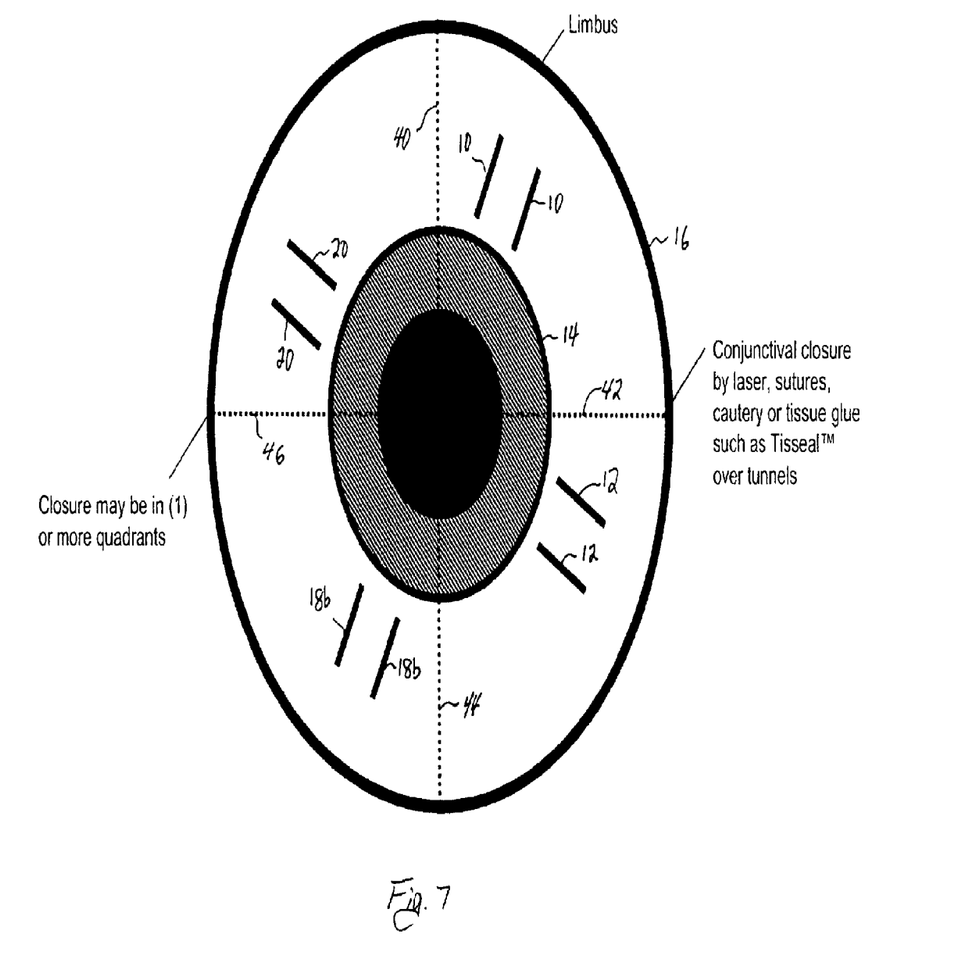
FIG. 7 depicts locations of manipulation of the conjunctival layer in accordance with an exemplary implementation of the present invention.

Care may be taken when moving the conjunctiva to attenuate tissue damage, such as de-vascularization and/or necrosis, resulting from, for example, excessive movement of the conjunctiva. In certain embodiments, portions of the conjunctiva to be moved may be separated from underlying tissue using known techniques, to thereby facilitate greater movement of the conjunctiva while controlling tissue damage. FIG. 7, discussed infra, depicts exemplary locations 40, 42, 44 and 46 of manipulation of the conjunctival layer.

Following removal of all or parts of the conjunctival layer, a number (e.g., eight) of inter-muscular limbal markings may be formed at locations corresponding to the planned placement locations of tunnel ablations in the sclera. If needed, cautery may be used for hemostasis. Also, if needed, the surgeon may form one or more of the marks once again to map tunnel ablation (e.g., incision) locations in each quadrant. Two radially orientated marks can be formed in a quadrant area 0.75 mm from the surgical limbus (the point where the iris can no longer be seen through the cornea), with each of the two marks being extended about 5-6 mm in length posteriorly and stopping anteriorly to the pars plana and with a 2 mm separation between each mark.

Two corresponding tunnel ablations in the marked quadrant area can then be generated, wherein scleral tissue is ablated to about 95% of a total thickness (e.g., approximately 500-550 microns) of the sclera. The incisions can be generated using an Er, Cr:YSGG laser having a frequency of 30 Hz, a wavelength of 2.78 microns, and a spot size of 900 microns. The surgeon can watch for the characteristic dark blue hue of choroid as an endpoint during each ablation process. The above-described steps can be repeated to generate additional pairs of incisions in the remaining three quadrant areas.

Subsequently, each of the treated sites can be closed with bipolar forceps, lasers, sutures, cautery, surgical tacks, or staples, followed by placement of 1 drop NSAID and 1 drop antibiotic thereto. Removed or affected areas corresponding to tunnel ablations may also be filled-in by a surgeon with any known biocompatable material, such as, for example, Tisseal, anti-inflammatories or antibiotics. In accordance with one aspect of the invention, removed or affected areas corresponding to tunnel ablations may be filled-in, partially or substantially completely, by the body (e.g., via the body's natural response) with sub-conjunctiva tissue. Generally, tunnel ablations can have widths that vary according to different rigidity factors and scleral thicknesses in different patients. However, incisional scleral depths of tunnel ablations that are greater than 90% may, in certain implementations, remain constant. After completing the tunnel ablations and closing/filling them, the conjunctiva can then be sutured back into position (cf. FIG. 7). An eye patch or patches may be used only if needed, and the patient can be instructed to use his or her eyes for normal near and far vision immediately following surgery.

In accordance with an aspect of the present invention, tunnel ablations may be applied to surface areas of the sclera disposed between the superior rectus muscle, medial rectus muscle, inferior rectus muscle, and lateral rectus muscle. The rectus muscle, medial rectus muscle, inferior rectus muscle, and lateral rectus muscle are typically disposed at the 0, 90, 180, and 270 degree angular locations of the eye. Exemplary groupings of tunnel ablations are shown in FIG. 1, wherein the exemplary groupings can be described in accordance with a polar coordinate system. Regarding the polar coordinate system, for reference, a center of the pupil can be designated as the pole and a line corresponding to the 3 o'clock orientation can be designated as the polar axis (e.g., zero degrees).

In the illustrated embodiment of FIG. 1, tunnel ablations are applied in a treatment zone that is defined between an inner radial dimension 14 and an outer radial dimension 16. The inner radial dimension 14 may coincide, for example, with the surgical limbus of the eye. In representative procedures, the inner radial dimension 14 corresponds to a zone that is about 0.75 mm outside of the surgical limbus. Typically, the inner radial dimension 14 will be disposed from about 0.75-1.0 mm outside of the surgical limbus, and both the inner radial dimension 14 and the outer radial dimension 16 will be disposed on the sclera.

A first set or grouping of tunnel ablations 10, a second grouping of tunnel ablations 12, areas 18a corresponding to a third grouping of tunnel ablations 18b (FIG. 2a), and a fourth grouping of tunnel ablations 20, are shown disposed on and in the sclera. One or more of these tunnel ablations may be modified, combined or duplicated, in whole or in part, in various ways, to cover or be disposed between portions of, as presently illustrated with reference to FIG. 1, the sclera between the superior rectus muscle, medial rectus muscle, inferior rectus muscle, and lateral rectus muscle. For example, a procedure may comprise the placement of groupings of tunnel ablations between each of the open areas formed between the superior rectus muscle, medial rectus muscle, inferior rectus muscle, and lateral rectus muscle disposed at, for example, the 270, 0, 90 and 180 angular positions.

In a typical implementation, although not required, the first set of tunnel ablations 10, second set of tunnel ablations 12, areas 18a corresponding to the third set of tunnel ablations 18b (FIG. 2a), and fourth set of tunnel ablations 20, are symmetrically formed relative to each other and are centered between the superior rectus muscle, medial rectus muscle, inferior rectus muscle, and lateral rectus muscle. According to the illustrated embodiment of FIG. 1, eight tunnel ablations 10, 12, 18a (locations), and 20, are disposed in the sclera at the 315, 45, 135, and 225 angular positions.

Figure 2A:
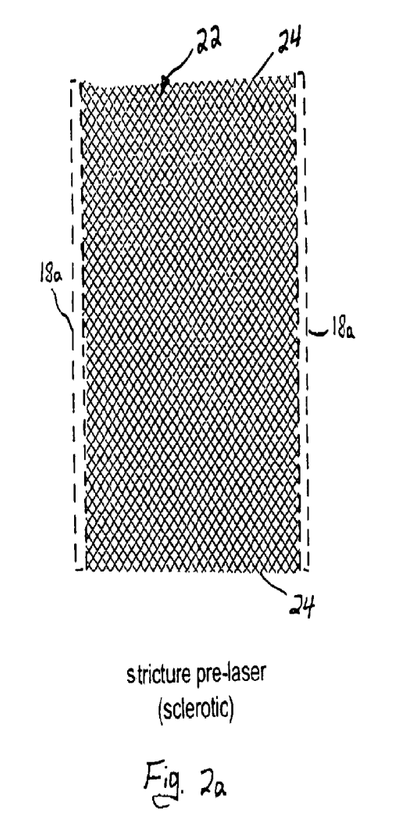
FIG. 2a is an enlarged view of a portion of scleral tissue in the eye of FIG. 1 that is suffering from a presence of strictures.
Figure 2B:
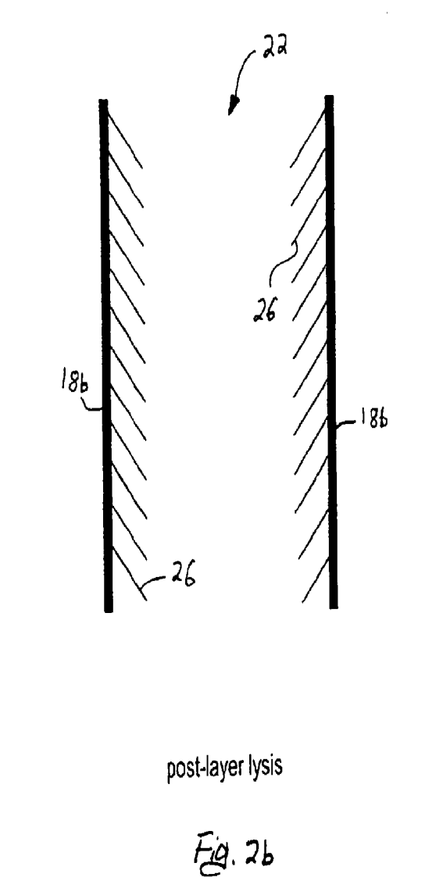
FIG. 2b is a view of the portion of scleral tissue shown in FIG. 2a, following formation of a pair of tunnel ablations within the sclerotic tissue by way a laser tunneling procedure in accordance with the present invention.

FIG. 2a is an enlarged view of a portion 22 of scleral tissue of the eye shown in FIG. 1 that is suffering from a presence of strictures within the scleral matrix. The locations 18a correspond to ideal potential candidates for the impartation of tunnel ablations to release strictures 24 within the portion 22 of the scleral tissue. The portion 22 of scleral tissue shown in FIG. 2b corresponds to the scleral tissue shown in FIG. 2a following formation of a pair of tunnel ablations 18b within the sclerotic tissue matrix by way a laser tunneling procedure in accordance with the present invention. The lines 26 can be considered to represent linkages of strictures within the sclera that have been at least partially released. Impartation of the tunnel ablations 18b into the sclerotic tissue thus can be seen to cause a releasing of the strictures 26, thereby allowing the cornea to steepen centrally to enhance an accommodation of the eye.

Figure 3:
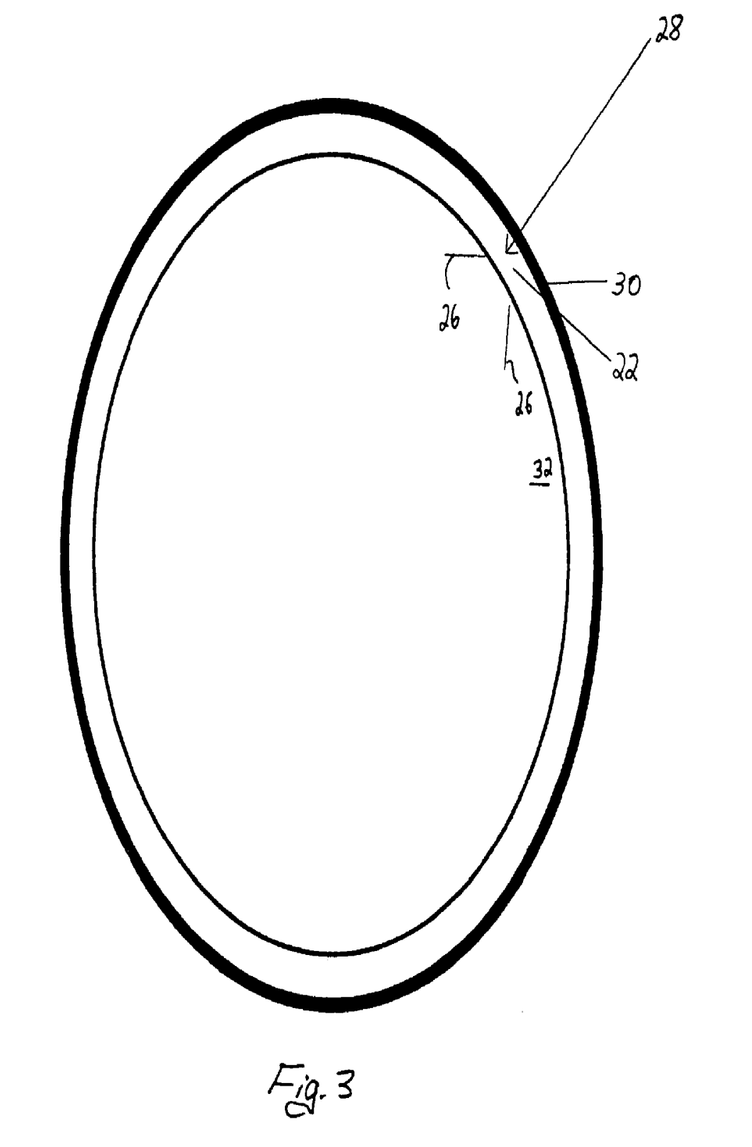
FIG. 3 is a cross-sectional view of the eye, depicting the application of energy to a sclerotic stricture area within the sclera of the eye.
Figure 4A:
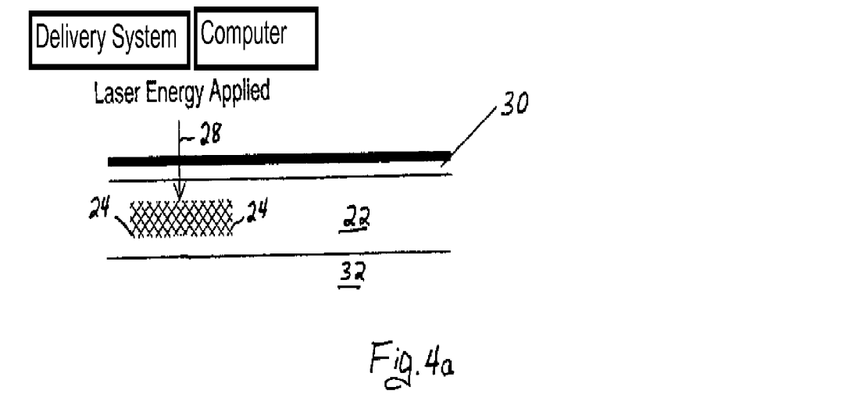
FIG. 4a is an enlarged view of the sclerotic stricture area shown in FIG. 3.

In the cross-sectional view of the eye depicted in FIG. 3, an application of energy 28, such as laser energy as described herein, is applied to the portion 22 of the scleral tissue, which has become sclerotic and stricture affected, within the sclera of the eye between a conjunctiva 30 and a choroid 32. FIG. 4a is an enlarged view of the sclerotic portion 22 of the scleral tissue shown in FIG. 3 and containing an age-accumulated concentration of elasticity-compromising strictures 24. Energy 28 is applied in the context of a laser tunneling procedure to facilitate formation of a tunnel ablation within the sclerotic tissue matrix in accordance with the present invention. According to a particular implementation, a beam (e.g., a collimated beam) of ablating optical energy may be directed through a majority or more of the thickness of the sclera, whereby tissues of the sclera are ablated along the path of the collimated beam.

Figure 4B:
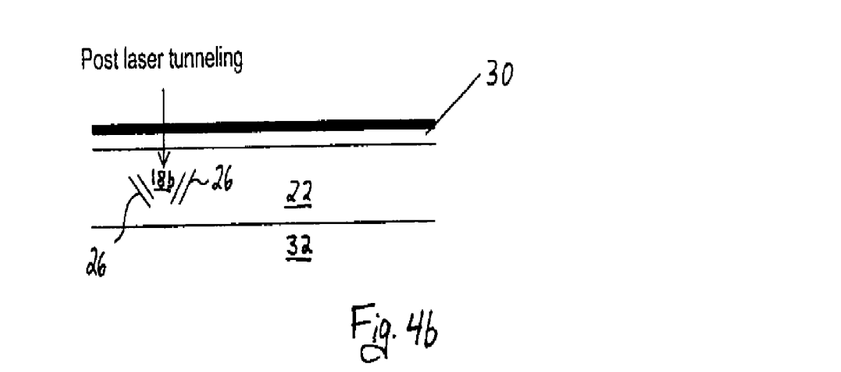
FIG. 4b is a view of the sclerotic stricture area of FIG. 4a, following formation of a tunnel ablation therein by way of a laser tunneling procedure whereby strictures are released according to an aspect of the present invention.

The sclerotic, stricture-containing portion 22 of scleral tissue from FIG. 4a is shown in FIG. 4b, following formation of a tunnel ablation within the scleral matrix 22 by way of a laser tunneling procedure according to an aspect of the present invention. In the present and or other embodiments, a maximum width, measured at the scleral surface, of a tunnel ablation can range from about 0.1 mm to about 1.5 mm, with a preferred maximum width ranging from about 0.9 mm to about 1.5 mm. A maximum depth dimension can range from greater than 90% (i.e., 91%) of the scleral thickness to the full (i.e., 100%) scleral thickness, with a preferred maximum depth ranging from about 92% of the scleral thickness to the full scleral thickness. The greatest treatment effect can typically be obtained when the tunnel ablations are formed to extend through all of the scleral thickness.

Following formation of a tunnel ablation within the scleral matrix 22 by way of a laser tunneling procedure, strictures are released according to an aspect of the present invention. The lines 26 are provided as a visualization of the surgical releasing of the constricted tissues, allowing the tissues an ability to resume previously lost physiological functions. These lines symbolically correspond to treated tissues of the sclera, and do not indicate the shape of the tunnel ablation which has been formed within the sclera.

The sizes (e.g., depths), shapes (e.g., bottom surfaces) and locations (e.g., spacing between sets) of the tunnel ablations may vary, and may be dependent upon, for example, the "mapping" of the eye. The age of the patient, level of sclerosis of the scleral tissue (i.e., which can be determined by a detection or determination of the severity of the presence of strictures and/or the commensurate loss of scleral tissue elasticity), size of the patient's eye, location of the patient's rectus muscles, size of the pupil, depth of the patient's sclera and/or the quality of the tissue surrounding the proximal adjacent choroid, can be important determinants in the development of a surgical intervention protocol for treating presbyopia with the tunnel ablations of the present invention. Certain implementations of the present invention comprise a step or steps of identifying, detecting or determining one or more of the depth of the patient's sclera, the level of sclerosis of the scleral tissue, the severity of the presence of strictures in the scleral tissue, the loss of scleral tissue elasticity, the size of the patient's eye, the location of the patient's rectus muscles, the size of the pupil, and the quality of the tissue surrounding the proximal adjacent choroid. These steps can be implemented in order, for example, to achieve a greater level of success in the treatment of presbyopia. In certain examples, the sclera depth, which can vary between patients and which can be identified prior to treatment, can be a determining factor. For instance, a patient with a sclera depth of 500 microns may require or benefit most from tunnel ablations formed with a pulsed Er, Cr:YSGG laser, having an 850 micron spot size, to extend all of the way through the sclera, whereas a patient with a sclera depth of 750 microns may require or stand to benefit the most from tunnel ablations extending 100% through the scleral and formed with a pulsed Er, Cr:YSGG laser having a 1000 micron spot size. In one example, the pattern of tunnel ablations is determined by the size of the patient's eye, the location of the patient's rectus muscles, the size of the patient's pupil, the depth of the patient's sclera, and the level of presbyopia prior to treatment.

While the depth of formation of the tunnel ablations will typically remain between 91% and 100%, it can be adjusted (e.g., within this range) based upon one or more of the mentioned considerations. Moreover, the width of the tunnel ablations can be tailored on a case-by-case basis, based upon these parameters. For example, in an example wherein the level of strictures is high and the quality of the tissue surrounding the proximal adjacent choroid is good (e.g., is sufficiently normal to be expected to be able to withstand impartation of the tunnel ablations without hypotonia), the tunnel ablations may be designed to form a pattern of tunnel-ablation sets (e.g., such as the pattern shown in FIG. 1) with a depth of about 100% of the scleral tissue and a width of about 1 mm measured at the scleral surface, wherein, furthermore, the bottoms of the tunnel ablations may comprise u-shaped or flattened bottoms (e.g., having a radius of curvature greater than about 75 mm). For example, in an instance wherein the level of strictures is relatively moderate and the quality of the tissue surrounding the proximal adjacent choroid is acceptable (e.g., not likely to cause hypotonia upon impartation of the tunnel ablations), the tunnel ablations may be designed to form a pattern of tunnel-ablation sets (e.g., such as shown in FIG. 1) with a depth of about 100% of the scleral tissue and a width of about 0.1 to 1.5 mm measured at the scleral surface; furthermore, the bottoms of the tunnel ablations may comprise u-shaped or flattened bottoms (e.g., having a radius of curvature greater than about 75 mm). In other examples, various combinations of the above parameters may be implemented, with lengths of the tunnel ablations being, for example, about 5 mm for moderately strictured scleras and about 6 mm for more highly strictured scleras.

Figure 5:
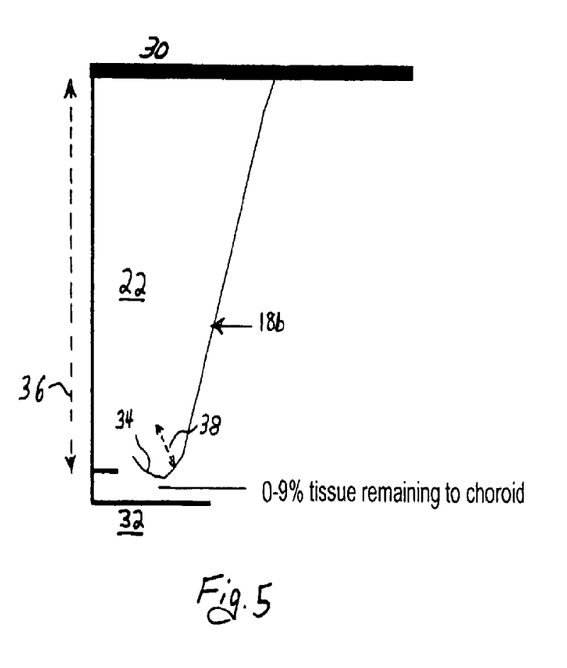
FIG. 5 is a cross-sectional view of a tunnel ablation formed within the sclera between the conjunctiva and the choroid of an eye.

FIG. 5 is a cross-sectional view of a tunnel ablation 18b formed within the sclera 22 between the conjunctiva 30 and the choroid 32 of an eye. The tunnel ablation 18b can have a width, measured on a surface of the sclera corresponding to an interface between the conjunctiva 30 and the sclera 22, greater than about 0.8 mm. The width can be measured in a direction parallel to the surface of the sclera 22. Furthermore, the tunnel ablation 18b can be formed to have a length on the surface, measured in a direction parallel to the surface, between about 5.25 mm and about 6.0 mm.

Moreover, according to certain implementations of the present invention, as a result of the tunnel ablations having one or more properties of being deeper, wider, and shaped differently, compared to prior art incisions, to thereby maximize expansion and minimize unwanted healing, as discussed below, sets (e.g., pairs) of adjacent tunnel ablations should be formed to have an initial spacing between one another (e.g., within the pair) of at least 2 mm.

Generally, according to an aspect of the present invention, tunnel ablations within a set can be formed to comprise elongated arcs or lines. According to illustrated embodiments, in addition to being disposed about 0.75 mm from the surgical limbus, the tunnel ablations can be marked or initially formed to be separated one from another by at least 2 mm, measured at the scleral surface. In these or other embodiments, the tunnel ablations should, according to a broad aspect of the present invention, have widths greater than 0.4 mm and, preferably, greater than 0.8 mm, measured at the scleral surface. The elongated tunnel ablations within a set can also be formed to be substantially parallel to one another and to be separated, following formation, by a distance of 1.8 to 1.2 mm. For instance, in certain implementations, when the laser energy ablates the scleral strictures during formation of tunnel ablations, a physiological expansion can typically occur naturally that causes the tunnel ablations to increase in width by up to about 50% of the initial lased width. Thus, initial tunnel-ablation widths (e.g., marked widths) of 0.4 to 1.6 mm, coupled with initial separations of about 2 mm between adjacent tunnel ablations in a set, can result in post-ablation widths of 0.6 to 2.4 mm and final separation distances of 1.8 mm to 1.2 mm, measured at the scleral surface. In similar examples with initial separations of about 2.5 mm between adjacent tunnel ablations in a set, post-ablation widths will of course be even greater.

In other embodiments, a surgical scalpel (e.g., diamond blade) may be used to form the tunnel ablations having depths as previously discussed in connection with fiber optic tip embodiments. According to certain aspects of the invention, regardless of the means used to form the tunnel ablations, it can be very important that the shapes of the bottom surfaces be rounded or flattened rather than v-shaped so that the patient does not experience unwanted regression following the procedure. Thus, in the case of, for example, a scalpel, care can be taken to ensure that bottom surfaces of the scalpel-formed tunnel ablations have u-shapened or flattened surfaces.

In accordance with typical implementations, the tunnel ablation 18b extends from a surface of the sclera 22 all of the way down through the sclera 22 to the choroid 32, or extends, as shown, to an area within the sclera 22 just shy of the choroid 32 boundary. For instance, the tunnel ablation 18b can extend a depth 36 of, for example, 500-600 microns into the sclera 22. According to an aspect of the present invention, the tunnel ablation 18b extends through significantly more than 90% of the thickness of the sclera 22, so that 0-9% of the sclera remains between a bottom surface 34 of the tunnel ablation 18b and the choroid 32.

By ablating to the 91-100% levels, the scleral strictures are treated for a maximum expansion and for a minimized chance of counter-productive healing, whereby a minimized likelihood of regression in presbyopic vision can be realized in long term follow-up observations of patients versus less deep incisions in the scleral which do not allow for maximum expansion or longevity of successful presbyopic treatments. As a result of the techniques disclosed herein, embodiments comprising a tunnel ablation 18b extending all of the way through the thickness of the sclera 22 do not cause hypotonia of the eye.

According to an aspect of the present invention, the tunnel ablation 18b comprises a u-shaped or flattened bottom surface 34, as distinguished from a v-shaped bottom surface. Thus, as distinguished from an incision that may be formed from a beam having a smaller spot size and/or with a different wavelength or power than that of the preferred Er, Cr:YSGG laser, which introduces an element of thermal necrosis, tunnel ablations of the present invention comprise "rounded" or "tunnel shaped" bottom surfaces rather than v-shaped bottom surfaces. According to one aspect of the present invention, implementation of, for example, an Er:YAG laser to form the tunnel ablation can result in a less rounded or less tunnel-shaped, and more of a v-shaped, bottom surface. According to another aspect of the present invention, implementation of, for example, an Er:YAG or other laser with a spot size of 0.8 mm or less to form the tunnel ablation can result in an even less rounded or less tunnel-shaped, and more of a v-shaped, bottom surface. By forming a u-shaped or flattened bottom surface, the scleral strictures are treated for a maximum expansion and for a minimized chance of counter-productive healing, whereby a likelihood of regression in presbyopic vision can be minimizing in patients post-treatment, as compared to that obtainable with the use of v-shaped incisions that do not allow for maximum expansion or longevenous presbyopic treatments.

In certain implementations of the invention, ablating to the 91% or greater level, and tunneling (i.e., forming enlarged bottom surfaces possessing one or more of enlarged widths and u- or flattened shapes), can better assure maximum treatment results with the greatest level of safety and least chance of regression in the patient.

One aspect of the present invention defines the bottom surface 34 to have a radius of curvature that is greater than about 75 mm. Certain embodiments of the present invention can comprise bottom surfaces 34 having radii of curvature 38 between about 75 and 90 mm, and other embodiments can comprise radii of curvature greater than 90 mm. The structures shown in FIG. 5 are not drawn to-scale in certain implementations of the present invention. However, in other implementations, one or more of the shapes or partial shapes of the illustrated structures in this figure, such as the tunnel ablation 18b, is/are defined to be drawn to-scale. In an implementation wherein the depth 36 and the shape of the tunnel ablation 18b are denoted to be drawn to-scale, a depth 36 of about 500 microns in the figure yields a radius of curvature 38 of the bottom surface 34 of about 75 mm. Similarly, a depth 36 of about 500 microns in the figure denotes a bottom-surface 18b radius of curvature 38 of about 90 mm when the depth 36 and the shape of the tunnel ablation 18b are denoted to be drawn to-scale.

Figure 6A:
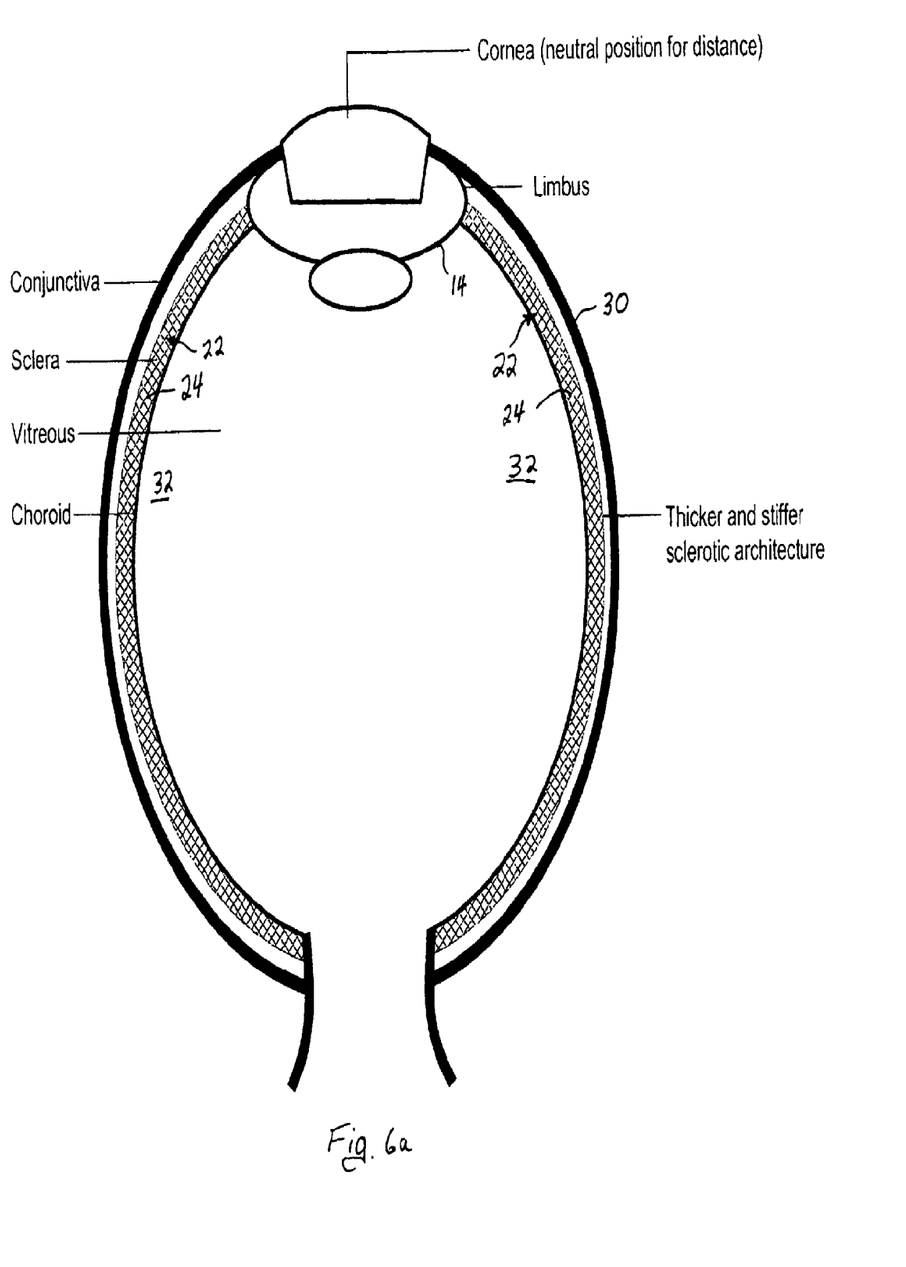
FIG. 6a shows a pre-operative shape of the central cornea of the eye in relation to an axial length of the eye.
Figure 6B:
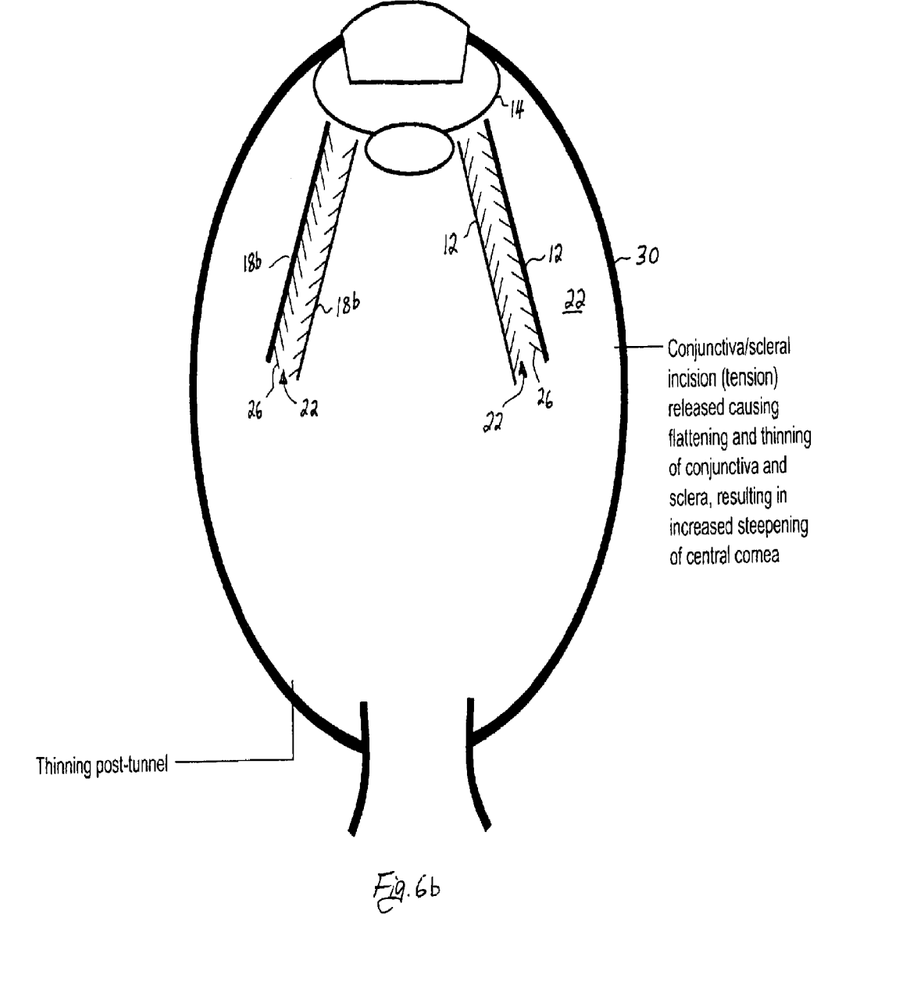
FIG. 6b depicts the structure of FIG. 6a following impartation of tunnel ablations, whereby steepening of the central corneal is effectuated along with thinning of the sub-conjunctival and scleral layers.

A schematic representation of an exemplary pre-operative shape of the central cornea of the eye in relation to an axial length of the eye is shown in FIG. 6a. The same structural elements of FIG. 6a are shown in FIG. 6b following impartation of a tunnel ablation, whereby steepening of the central corneal is effectuated along with thinning of the sub-conjunctival and scleral layers. In FIG. 6b, an allowance for added steepening of the cornea is generated by way of the impartation of the tunnel ablations of the present invention, so that the eye is provided with an ability to refocus at near distances while maintaining an ability to focus at a distance. The release of sub-conjunctival strictures can attenuate the loss of near vision that typically occurs with age, to the extent caused, for example, by tissue sclerosis resulting in loss of elasticity of the sclera, cornea and related structures. The tunneling results in ablation of the strictures, allowing for or causing one or more of a forward prolapse and a steepening of the cornea. FIG. 7 depicts locations 40, 42, 44 and 46 of manipulation of the conjunctival layer (e.g., before and after impartation of the tunnel ablations) in accordance with an exemplary implementation of the present invention.

Regarding configurations of the source of ablation, the parameter ranges of the source of ablation (e.g., laser) can, in exemplary embodiments, be dependent upon desired, predetermined or expected lengths, widths and/or depths of tunnel-ablation incisions. A mapping can determine the location, pattern, shape and landscape of the region acquiring the treatment based on, for example, rigidity, concentration of strictures, muscle contraction, and accommodation. The treatment energy beam can be completed by contact or non-contact of the laser energy in a pulse mode, or CW mode, that is proximal to the treatment area using, for example, a fiber based delivery system. For example, tunnel ablations formed with depths approximating the thickness of the sclera (e.g., about 100%) may be generated with relatively high power densities and/or may have relatively large widths (e.g., 1 mm, measured at the scleral surface), and in further examples, these tunnel ablations may have u-shaped or flattened bottoms (e.g., having a radius of curvature greater than about 75 mm). In modified implementations, tunnel ablations formed with depths approximating the thickness of the sclera (e.g., about 100%) may be generated with relatively high power densities and/or may have widths ranging from 0.1 to 1.5 mm, measured at the scleral surface, and in further such modified embodiments, these tunnel ablations may have u-shaped or flattened bottoms (e.g., having a radius of curvature greater than about 75 mm).

Scleral structures having relatively advanced presbyotic conditions (e.g., augmented tissue sclerosis with commensurate stenosis-induced loss of accommodation) will typically stand to benefit from greater degrees of tunnel-ablation treatments. The degree of tunnel-ablation treatments can be increased by forming the tunnel-ablations in any one or more of greater numbers, greater densities, greater widths, greater depths, more u-shaped or flattened bottom surfaces, and greater lengths. A patient's sclera that is suffering from substantial stenosis will typically stand to benefit from tunnel ablations of greater widths and depths, as compared to scleral structures of a patient's sclera that is less stenotic. Stenotic scleral tissues will typically correspond to those of older patients. Dye enhancement can be used to convey the degree of, and/or the location(s) of, the fibrotic scleral material or the relatively greater concentrations of stenotic tissue of a sclera. Tunnel ablations can then be designed to intersect with those locations. Additionally, or alternatively, any known means for determining or measuring the tissue elasticity of the sclera, or the accommodation of the patient's eye, can be implemented to facilitate a determination of the degree of tunnel ablations needed for treatment. As known, such means can include computers. In addition to a degree of stenosis of potential treatment areas of a patient's sclera, the size of the patient's eye and/or the physical condition (e.g., ability to respond favorably to the surgery) can factor in to help determine the degree of tunnel-ablation treatments to be administered. Characteristics of the eye muscles, such as their location, may also play a role in determining shapes and/or locations of the tunnel ablations that may be required.

Sets or groupings of tunnel ablations may be formed manually and/or with the aid of automated devices, such as computer (FIG. 4a) controlled or aided scanners (e.g., having articulated arms) known to those skilled in the art. As known, computers contain microprocessors. The treatment energy beam can be completed by contact or non-contact of the laser energy in a pulse mode, or CW mode that is proximal to the treatment area using a scanner based delivery system (FIG. 4a) with a predetermined software pattern or template. As known, delivery systems embody apparatus and waveguides for propagating energy and formed with proximal ends and distal ends that output the energy. Software can be utilized to implement patterns of tunnel ablations based upon parameters of the eye, such as the mapping of the eye as discussed above.

Regarding formation by manual means, an output, such as, for example, a fiber optic tip in cases where the treatment is electromagnetic energy, may be used to focus electromagnetic (e.g., optical) energy onto the sclera in order to form tunnel ablations to depths of, for example, about 91% to about 100% of the sclera thickness (e.g., about 500 microns to 700 microns). An exemplary implementation can comprise an Er, Cr:YSGG laser with a 900 micron quartz or sapphire (contact) tip operated at 2 W and 2.78 microns. Regarding formation by automated scanning, such scanning can be performed to achieve the formation of one or more tunnel ablations in predefined formations and locations of the sclera as described herein and known to those skilled in the art, and/or beneficially applied to treatment of a relatively large portion of the sclera wherein, for example, all of the desired tunnel ablations may be automatically formed by the scanner during a single procedure. An optical system for automatically providing treatment energies to the sclera may comprise an ablative laser having a predetermined wavelength and being focused by, for example, a lens which is directed, for example, onto a scanner for patterning (e.g., using a mirror) a predetermined treatment energy onto the patient's eye to form one or more tunnel ablations. The scanner may comprise motorized mirrors and/or a refractive optical means such that laser energy is delivered (e.g., scanned) to the eye in the predetermined patterns.

The contents of all cited references, including literature references, issued patents, published patent applications, and co-pending patent applications, cited in this application and in the provisional patent application upon which priority is claimed, are hereby expressly incorporated by reference. The above-described embodiments have been provided by way of example, and the present invention is not limited to these examples. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, it is intended that the present invention not be limited by the disclosed embodiments, but be defined by reference to the appended additional disclosure in claims format.

What is claimed is:

1. A surgical system for treating an eye in need of a physiological or vision correction, comprising:
    a source of treatment energy for cutting or ablating an anatomic structure of an eye;
    a measuring device for facilitating a determination of a thickness of the anatomic structure; and
    a delivery system having an output end configured to facilitate delivery of treatment energy from the source to an area of the anatomic structure in need of a physiological or vision correction;
    wherein the delivery system responds to the measuring device by ablating more than 90% of the thickness of the anatomic structure, but not an underlying structure, to form a tunnel ablation; and
    wherein the output end (a) provides a spot size of 0.8 mm or less and (b) applies a wavelength and power corresponding to the tunnel ablation having a bottom surface with a u-shape or a flattened bottom and a radius of curvature less than about 75 mm.

2. A surgical system as defined in claim 1, wherein the source of treatment energy comprises an Er:YAG laser.

3. A surgical system as defined in claim 1, wherein the spot size is in a range with a low end at about 0.4 mm.

4. A surgical system as defined in claim 1, wherein the output end has a fiber tip and a tapering shape with a distal output surface perpendicularly disposed relative to a longitudinal axis of the fiber tip.

5. The surgical system as set forth in claim 4, wherein the tapering shape is conical.

* * * * *